United States Patent [19]

Hikuma et al.

[11] 4,297,173

[45] Oct. 27, 1981

[54] METHOD FOR DETERMINING AMMONIA AND SENSOR THEREFOR

[75] Inventors: Motohiko Hikuma; Tatsuru Kubo; Takeo Yasuda, all of Yokohama; Isao Karube, Tachikawa; Shuichi Suzuki, Tokyo, all of Japan

[73] Assignee: Ajinomoto Company, Incorporated, Tokyo, Japan

[21] Appl. No.: 152,177

[22] Filed: May 22, 1980

[51] Int. Cl.$^3$ .................... C12Q 1/00; G01N 27/30
[52] U.S. Cl. ............................ 204/1 T; 23/230 R; 204/195 P; 204/195 B; 422/68; 435/29; 435/37; 435/182; 435/288; 435/817
[58] Field of Search ........... 204/1 N, 1 P, 1 E, 195 B, 204/195 P; 435/37, 25, 26, 28, 29, 182, 288, 817; 128/635; 23/230 R; 422/68

[56] References Cited

U.S. PATENT DOCUMENTS 4,216,065  8/1980  Rechnitz et al. .................. 204/1 T

OTHER PUBLICATIONS

R. K. Kobos et al., Anal. Letters, vol. 10, No. 10, pp. 751–758, (1977).
Michael J. Pelczar, Jr. et al., "Microbiology", pp. 702–704, (1972).
Wolfgang K. Joklik et al., "Microbiology", 15th Edition, p. 58, (1972).
Isao Karube et al., Biotech. & Bioengineering, vol. 19, pp. 1535–1547, (1977).
Isao Karube et al., J. Ferment. Technol., vol. 55, No. 3, pp. 243–248, (1977).
G. A. Rechnitz et al., Analytica Chimica Acta., vol. 94, pp. 357–365, (1977).
K. Venkatsubramanian, "Immobilized Microbial Cells", Chapters 14 and 15, (1979).
R. K. Kobos et al., Anal. Chem., vol. 51, No. 8, pp. 1122–1125, (1979).

Primary Examiner—G. L. Kaplan
Attorney, Agent, or Firm—Oblon, Fisher, Spivak, McClelland & Maier

[57] ABSTRACT

The concentration of ammonia in an aqueous liquid is determined by contacting a sample of the liquid with dissolved oxygen and with a microbial electrode comprising an oxygen-sensitive electrode, a porous membrane, and nitrifying bacteria confined or immobilised by the membrane which are in direct or close contact with the diaphragm of the electrode. The rate of oxygen consumption under otherwise uniform conditions is as precise a measure of concentration of ammonia as a conventional colorimetric method and distillation-titration method.

15 Claims, 10 Drawing Figures

METHOD FOR DETERMINING AMMONIA AND SENSOR THEREFOR

BACKGROUND OF THE INVENTION

1. Field of the Invention

This invention relates to ammonia analysis, and more particularly to a method for determining ammonia concentration with a microbial electrode electrochemically.

2. Description of the Prior Art

Recently, it has been said that ammonia, one of the members of a nitrogen cycle in nature, becomes harmful to aquatic life and causes environmental pollution since it enriches the nutrition of lake and marshes and bays. A simple, quantitative and continuous determination method for ammonia which is suitable for the purpose of on-line measurement is strongly desired.

According to a conventional method, it is possible to determine the concentration of ammonia by distillation-titration methods and colorimetric method. However, these conventional methods are unsatisfactory for the purpose of on-line measurement since the titration method can be performed only manually and the colorimetric method usually requires a complicated filtration process to remove insoluble impurities from a sample solution.

According to another conventional method, ammonia can be determined electrochemically using an ammonia gas-sensitive electrode comprising a combined glass electrode and ammonia gas-permeable membrane. However, this conventional method is also unsatisfactory for on-line measurement since it is necessary to adjust the pH of the sample solution to above 11.0 in order to convert ammonium ions in the sample solution into volatile ammonia gas and this method is affected greatly by impurities such as amines, coexisting in the sample solution and with hydroxides of alkaline earth-metal precipitated from the sample solution under alkaline conditions.

Recently it has been reported that BOD of waste water may be determined with a microbial sensor comprising an oxygen-sensitive electrode and immobilized microorganisms with precision and reproducibility in the following literature references:

I. Karube et al; Biotechnol. Bioeng., 19, 1535 (1977)
I. Karube et al; J. Ferment. Technol., 55, 243 (1977)
K. Matsumoto et al; Anal. Chem. Acta 105, 429 (1979)
M. Hikuma et al; Biotechnol, Bioeng., 21, 1845 (1979).

SUMMARY OF THE INVENTION

The primary object of this invention is to provide a method for determining the ammonia concentration in an aqueous liquid which is simpler, no less precise and more suitable for on-line measurement than conventional methods.

It has now been found that an ammonia concentration in an aqueous liquid can be electrochemically determined with a microbial electrode comprising an oxygen-sensitive electrode, a porous membrane and fixed nitrifying bacteria.

DESCRIPTION OF THE PREFERRED EMBODIMENTS

According to the present invention, ammonia and ammonium ion in an aqueous liquid can be determined within 20 minutes with high precision and reproducibility. Ammonia and ammonium ion are referred to as ammonia in this invention. The method of the present invention lends itself to automatic operation and is suitable for continuous monitoring of ammonia in water and less affected with impurities than a conventional ammonia gas-sensitive electrode method.

In this method, the fixed microorganisms are in direct or close contact with the diaphragm of an oxygen-sensitive electrode. The fixed microorganisms and the oxygen-sensitive electrode together form the microbial electrode of the present invention.

Fixed microorganisms employed according to the present invention are those which are immobilized by trapping microbial intact cells between the diaphragm of the electrode and a porous membrane; or they may be dispersed in a continuous solid matrix of a material having the same properties such as collagen and other natural polymers. Porous membranes employed according to the present invention are those which are permeable to dissolved oxygen, ammonia gas or ammonium ion but impermeable to the immobilized microbial cells. For example, conventional dialysis membranes such as cellophan, acetyl cellulose membrane, semi-permeable membranes as Milipore filter (Trademark of Milipor Ltd. Co.), gas permeable membranes such as porous Teflon, Silicone (Trademark of Shinetsu-Kagaku Co., Inc.), polybutadiene and polyethylene membranes, and cation-permeable membranes such as Selemion ® membrane (Trademark of Asahi Glass Co., Inc.) are preferable. Among these membranes, gas, or cation-permeable membranes are more preferably employed since these membranes are impermeable to organic compounds such as sugar, amino acid, and organic acid which may bring about an undesirable contamination of the microbial electrode with other common microorganisms during long-term continuous determination.

Microorganisms employed according to the present invention include nitrifying bacteria such as nitrous acid-forming bacteria capable of oxidizing an ammonium ion or ammonia to form nitrous acid as follows:

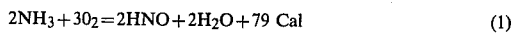

$$2NH_3 + 3O_2 = 2HNO_2 + 2H_2O + 79 \text{ Cal} \tag{1}$$

and a nitric acid-forming bacteria which are capable of further oxidising nitrous acid to nitric acid:

$$HNO_2 + O_2 = HNO_3 + 21.6 \text{ Cal.} \tag{2}$$

Examples of nitrifying bacteria are nitrous acid-forming bacteria such as *Nitrosomonas monocella*, *Nitrosococcus nitrosus*, *Nitrosospira briensis*, *Nitrososocystis javanensis*, *Nitrosogloea merismoides*, and nitric acid-forming bacteria such as *Nitrobacterwinogradski* and *Nitrocystis sarcinoides*.

According to a preferred embodiment of the present invention, the mixture of nitric acid-forming bacteria and nitrous acid forming bacteria are employed and the mixture of these bacteria can be easily obtained from the active sludge of water treatment plants by culturing the sludge in a conventional culture medium suitable for this kind of microorganisms and in this case individual identification of the microorganism is not required.

According to another preferred embodiment of the present invention, pure and identified nitrifying bacteria such as *Nitrosomonas europaea* ATCC 19718 and *Nitrobacter agilis* ATCC 14123 or their mixture are used.

These nitrifying bacteria are those which can grow without organic compounds by using a carbonate or bicarbonate as a sole carbon source and by utilysing energy derived from the above oxidizing reaction (1) and (2), and are known as autotrophic bacteria.

Nitrifying bacteria are cultured in a conventional culture medium containing carbonate such as $CaCO_3$, $MgCO_3$. Bacterial cells are then harvested by an entirely conventional method such as filtration, preferably together with insoluble $CaCO_3$ or $MgCO_3$, washed with water and stored at a low temperature. The number of microorganisms affects the observed rate of oxygen consumption and is not precisely reproducible. It is necessary, therefore, to fix an adequate number of cells, to establish the oxygen-consuming ability when in contact with sample having known ammonia concentration, and to compare the rate of oxygen consumption of the same microorganisms in contact with an unknown test sample with a calibration chart derived from the test on known standard sample.

The fixed microorganisms of the microbial electrode may be employed for long series of tests in the method of the present invention.

The oxygen-sensitive electrode employed according to the present invention can be of any conventional one such as galvanic or polarographic type oxygen-sensitive electrode.

Apparatus for performing the invention is shown in the appended drawings together with charts illustrating the operating characteristics of the apparatus. In the drawings.

In the following description, reference will be made by way of example to the accompanying drawings.

Figure 1:
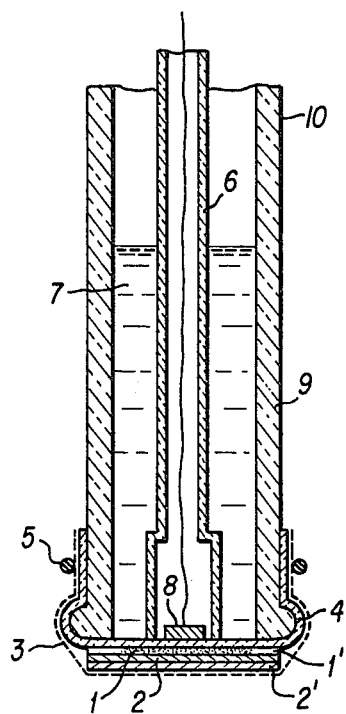
FIG. 1 is a simplified elevational section view of the microbial electrode indicated in EXAMPLE 1 equipped with a conventional oxygen-sensitive electrode.

FIG. 1 shows a microbial electrode 10 formed by smearing intact wet cells of nitrifying bacteria on a diaphragm membrane of the oxygen-sensitive electrode, and covering the microbial layer 1 with porous membrane 2 such as dialysis membrane 4 and Nylon net of which upper part is fastened with rubber band 5.

The microbial electrode further consists of vinyl patch (spacer) 1', an aluminum anode 6, saturated electrolyte (KCl) solution 7, a platinum cathode 8, and an insulator 9. In the electrode shown in FIG. 1, the nitrifying bacteria may be held between membranes 3 and 4 together with a porous membrane or like solid bodies 2 and 2' such as Millipore filter porous Teflon membrane and filter paper, or may be held in a polymer matrix such as collagen and polyacrylamide gel in the form of immobilized microorganisms. This method is preferable since the amount of intact cells used may be easily controlled and the microbial electrode thus obtained have uniform characteristics.

Figure 3:
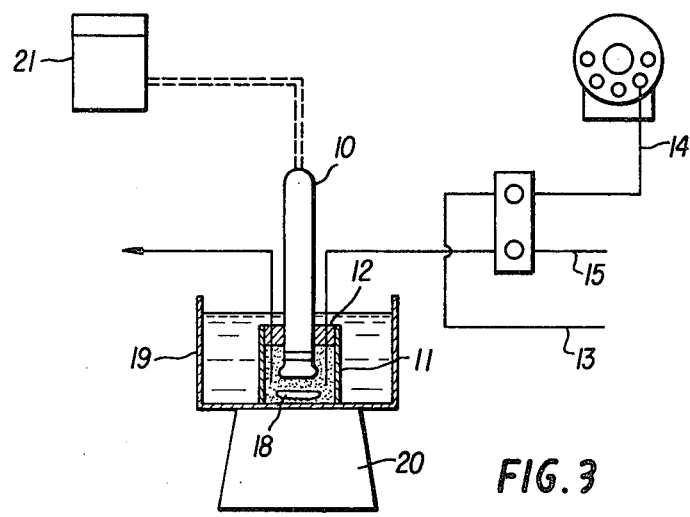
FIG. 3 is a schematic diagram of a continous determination system suitable for on-line measurement of ammonia concentration employing the microbial electrode of FIG. 1 or FIG. 2.
Figure 4:
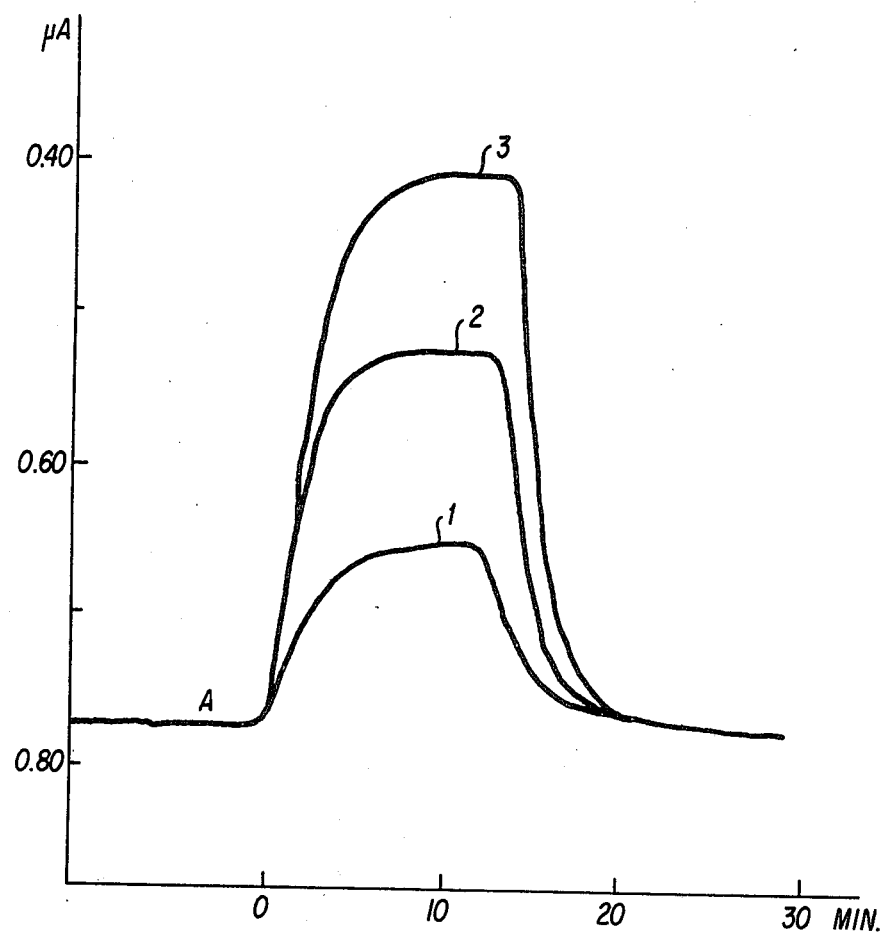
FIG. 4 shows the change of output current from the electrode of FIG. 1.

An example of schematic diagram of the continuous determination system of the invention is illustrated in FIG. 3. In FIG. 3, there are shown a microbial electrode 10, rubber packing 12 for fixing the microbial electrode 10, flow cell 11, magnetic stirrer 20 which turns a glass-coated steel bar 18, recorder 21, inlet for blow-in air 13, inlet for carrier solution 15, inlet for sample 14, and water jacket 19. In FIG. 3, distilled water or buffered water saturated with dissolved oxygen is fed into the flow cell 11 at a constant flow rate during the determination with the current of the electrode 10 recorded. After the current has attained a constant value (referred to as the "base current" or "base line") the sample solution is directly injected into the system by the auto sampler at a constant flow rate at a constant interval, dilluted by flowing carrier solution saturated with dissolved oxygen, and put into the cell 11 and stirred with the bar 18. The temperature of the flow cell 11 is maintained by the jacket 19 at a constant temperature in the range from 25° to 35° C. during the determination. When the sample solution is introduced into the flow cell and contacted with the microbial electrode, the current of the electrode which is visually recorded on the recorder 21 decreases markedly with time until it reaches a steady state, as illustrated in FIG. 4.

The time to reach a steady state is within 5 to 10 minutes. The decrease in current is caused by an uptake of dissolved oxygen by the fixed nitrifying bacteria of the electrode in the course of oxidizing ammonia.

The rate of the current decrease and the decrease in current in the steady state are proportional to the concentration of ammonia. Therefore, the concentration of the ammonia can be calculated from the rate of current decrease or the decrease in current in steady state by virtue of the linear relationship between them.

Since the rate of current is influenced by the pH and temperature, it is necessary to perform the determination procedure at a constant temperature ranging from 25° to 35° C. and a pH ranging from 6 to 12. When gas-permeable membrane is used, the pH of the solution in the flow cell is preferably kept above 9.0 since most ammonia molecules exist in the form of ammonium ion below pH 9.0 where they do not pass through the gas-permeable membrane.

The method of the present invention is not affected by other organic compounds and inorganic ions coexisting in the waste water or culture medium of various kind of fermentations since nitrifying bacteria of the microbial electrode do not respond to these impurities, and since the output of an oxygen-sensitive electrode is less effected by other impurities than that of an ammonia gas-sensitive electrode using a combined glass electrode.

As described above in detail, an extremely simple and continuous determination of ammonia in an aqueous liquid can be achieved with precision and reproducibility. This new method for determination will be useful for on-line measurement of ammonia in a water of lake and marshers, bay, waste waters, and in a culture medium of various kind of fermentations The invention will now be illustrated by the following Examples. In the Examples, % represents % W/V.

EXAMPLE 1

200 ml activated sludge (MLSS 5000 ppm) from a fermentation factory of Ajinomoto Co., Inc. containing nitrifying bacteria was inoculated into 2.5 liter culture medium shown in Table 1.

TABLE 1

| Composition of medium (pH 8.0) | |
|---|---|
| Component | Concentration |
| $(NH_4)_2SO_4$ | 0.06% |
| $K_2HPO_4$ | 0.05% |
| $CaCO_3$ | 1.0 % |
| $FeCl_3$ | 20 ppm |
| $MgSO_4.7H_2O$ | 50 ppm |
| $CaCl_2$ | 20 ppm |

Then, it was cultured in a 5.0 liter vessel under aerobic condition ($\frac{1}{2}$ V.V.M. aeration) at room temperature (20°~30° C.) for more than 4 months. The pH of the culture medium was controlled to 8.0 with 1 N $Na_2CO_3$ solution. Another fresh culture medium shown in Table 1, in which the concentration of $(NH_4)_2SO_4$ is 0.6%, was fed into the culture medium at a constant feeding rate of 200 ml/day.

The volume of the culture medium in the vessel was kept 2.5 liter during the cultivation. The cultured broth thus obtained contains nitrous acid-forming bacteria and nitric acid-forming bacteria (not identified) but do not contain other common microorganisms.

Then 5.0 ml cultured broth was filtured with the porous acetylcellulose membrane (Type HA of millipore, pore size; 0.45 μm, diameter; 47 mm, thickness: 150 μm), thereby the nitrifying bacteria were adhered on the membrane together with insoluble $CaCO_3$.

A microbial electrode 10 shown in FIG. 1 was obtained by attaching the membrane retaining the nitrifying bacteria carefully on the Teflon membrane of a Galvanic-type oxygen-sensitive electrode (Model 3021 of Denki Kagaku Keiki, Tokyo) so that the layer of the nitrifying bacteria were entrapped between the two membranes, covering with Nylon net and fixing the upper part of Nylon net with rubber ring 5.

The electrode 10 thus obtained were inserted into a flow cell 11 through a rubber packing to give a 5.0 ml-flow cell.

A continuous measuring system shown in FIG. 3 was assembled with the flow cell. For measurement, 0.01 M sodium borate solution (pH 8.8) containing 20 ppm chloramphenicol was saturated with dissolved oxygen by blowing air into it and was flowed into the flow cell at a flow rate of 3.9 ml/min. while blowing air into it at a rate of 3.9 ml/min. Thus, the oxygen saturated buffer solution runs in the flow cell as a carrier fluid. The inside temperature of the flow cell was adjusted to 30° C.±0.2° C. by passing warm water through the jacket 19. After the electric current of the electrode was stabilized, sample solutions containing various concentration of ammonium sulfate were injected at a rate of 0.8 ml/min. for 12 min. with 30 minutes interval, respectively and the results are shown in FIG. 4, in which the axis of abscissa shows time (minutes), the axis of ordinate shows the current (μA) and "A" represent a base line.

In this figure, 1, 2 and 3 show ammonia concentration of 0.44, 0.88 and 1.32 ppm respectively which were obtained by a conventional method of the Japanese Industrial Standard JIS K0102-1974. The current of the electrode began to decrease a few seconds after a sample was injected and reached a constant level (steady state) after about 8 minutes. In steady state, a rate of consumption of dissolved oxygen by nitrifying bacteria is in equillibrium with that of diffusion of the oxygen from sample solution into the membrane of the electrode. When the injection of sample was stopped, the current of the electrode turned back to the base line within 8 minutes.

Figure 5:
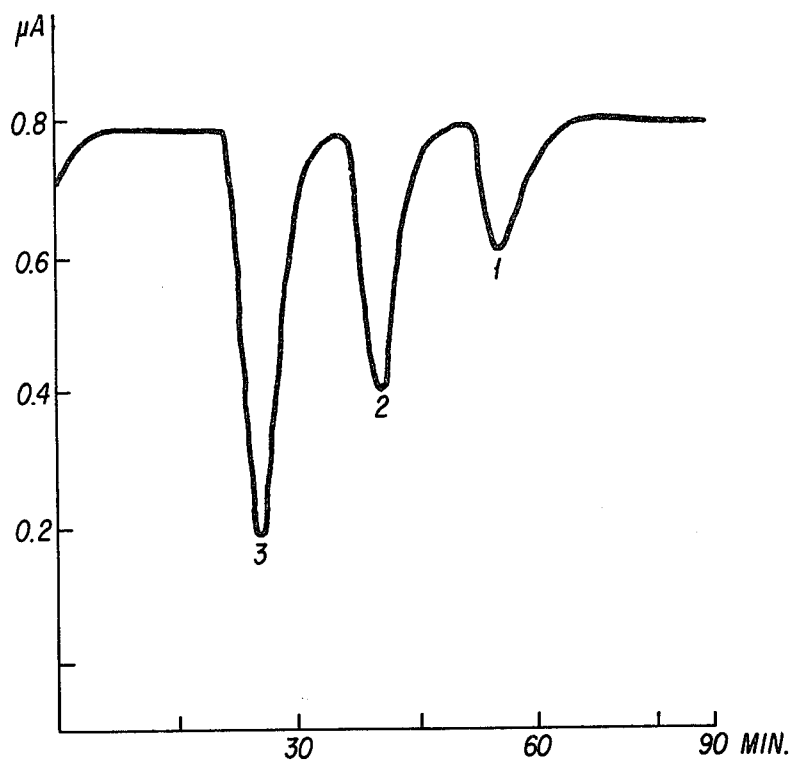
FIG. 5 is a chart indicating the relationship between the output current of the electrode of FIG. 1 ($\mu A$) and the ammonia concentration (ppm) when consecutively injecting various concentration of ammonia with a pulse width of 3 minutes into the flow cell of FIG. 3.
Figure 6:
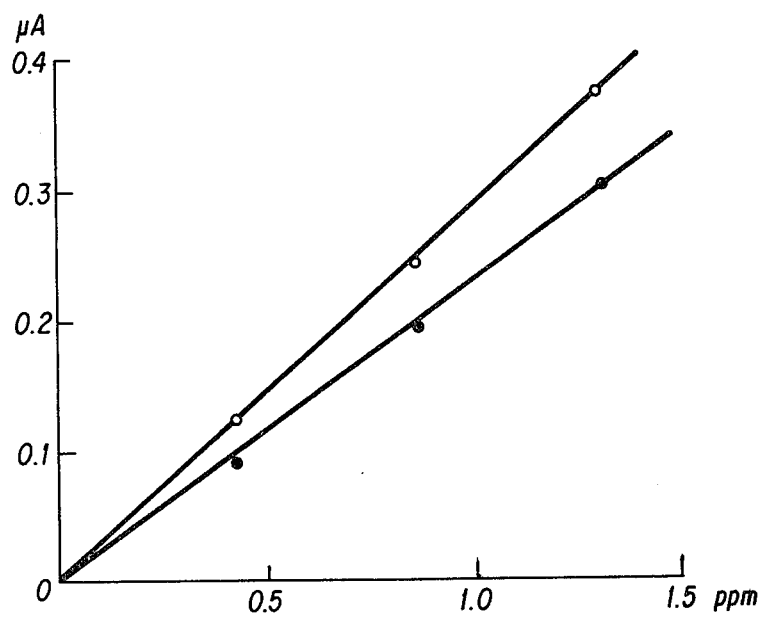
FIG. 6 is chart showing the relationship of the ammonia concentration (ppm) and the current decrease ($\mu A$) indicated in EXAMPLE 1.

FIG. 5 is a chart obtained by pulse method in which the same sample solutions were injected for 3 minutes with 12 minutes interval. Then the relationship both between the decrease in current in steady state and ammonia concentration and between the rate of current decrease (pulse method) and the concentration of ammonia were examined and the results are shown in FIG. 6. In this figure, the axis of abscissa represents ammonia concentration and the axis of ordinate represents the current decrease. The linear relationships are observed both between the current decrease in steady state and the concentration of ammonia (open circles in FIG. 6) and between the rate of current decrease (in pulse method) and the concentration of ammonia (black circles in FIG. 6).

Similar tests were carried out with organic compounds and inorganic salts shown in Table 2 to examine the selectivity of the microbial electrode and the results are shown in Table 2, in which it is shown that the microbial electrode of the present invention scarecely respond to these materials.

TABLE 2

| Selectivity of the electrode | | |
|---|---|---|
| Material | Concentration in flow cell (ppm) | Different current (μA) |
| Ammonia | 0.88 | 0.27 |
| glucose | 170 | 0.01 |
| Ethanol | 170 | " |
| Glutamic acid | 170 | " |
| Acetic acid | 170 | " |
| Sodium nitrite | 17 | " |
| Urea | 17 | 0.09 |
| Monomethyl amine | 17 | 0.01 |
| Diethyl amine | 170 | 0 |
| NaCl | 100 | 0 |
| $MgSO_4$ | 100 | 0 |
| $KH_2PO_4$ | 100 | 0.078 |

(*) sample solution was injected for 100 hours

For example, the sensibility of the electrode for glucose is below one thousanth.

Figure 7:
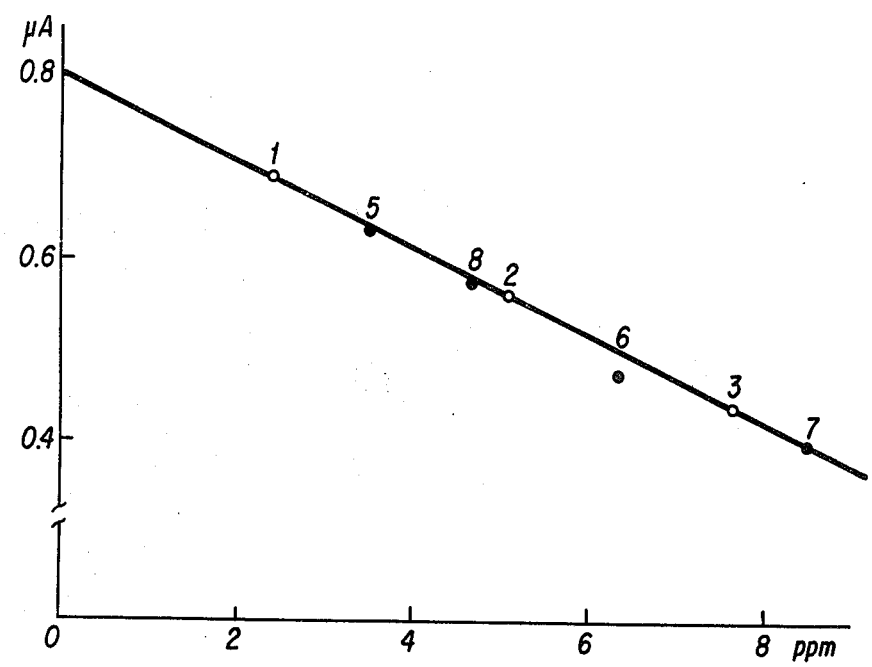
FIG. 7 is a chart showing the relationship of the ammonia concentration (ppm) and the current decrease ($\mu A$) indicated in EXAMPLE 1.

Four kinds of waste water from a fermentation factory of Ajinomoto Co., Inc. of which ammonia and BOD concentration are shown in Table 3 were diluted with water. A similar test was also performed with the diluted solution and the results are shown in FIG. 7.

TABLE 2

| Analysis values* of waste water | | |
|---|---|---|
| Sample No. | Concentration of free ammonia | B.O.D. |
| 5 | 3.51 (ppm) | 10.0 (ppm) |

TABLE 2-continued

| | Analysis values* of waste water | |
|---|---|---|
| Sample No. | Concentration of free ammonia | B.O.D. |
| 6 | 6.23 | 19.0 |
| 7 | 8.50 | 0.3 |
| 8 | 4.70 | 0.5 |

*these values were obtained by the Japanese Industrial Standard method JIS K0102-1974

In this figure, the black circles represent the results which are in good agreement with the values shown by the solid line corresponding to the open circles of FIG. 6

EXAMPLE 2

500 ml sterilized culture medium shown in Table 3 was put into 2 liter-flask together with 0.05 ppm of cresol red (pH indicator).

TABLE 3

| Composition of culture medium (pH 8.2) | |
|---|---|
| Component | Concentration |
| $(NH_4)_2SO_4$ | 0.3% |
| $KH_2PO_4$ | 0.05% |
| $FeCl_3$ | 20 ppm |
| $CaCl_2$ | 20 ppm |
| $CaCO_3$ | 1.0% (sterilized seperately) |
| $MgSO_4.7H_2O$ | 50 ppm (sterilized seperately) |

Then, nitrifying bacteria, *Nitrosomonas europaea* ATCC 19718, was inoculated into the culture medium and the flask was allowed to stand for 25 days at room temperature (25°~30° C.). When color of the culture medium changed yellow with nitrous or nitric acid produced by the nitrifying bacteria, 1 N-$K_2CO_3$ solution was added to the culture medium to keep the pH constant.

50 ml cultured broth thus obtained was filtered with the Millipore filter (Type HA, diameter: 47 mm, Millipore Ltd.). Then a microbial electrode as illustrated in FIG. 1 was assembled by the same manner as described in Example 1.

The porous acetyl cellulose membrane 2 retaining the nitrifying bacteria 1 was cut into a circle and (diameter: 47 mm) attached on the surface of a Teflon membrane of an oxygen-sensitive electrode 4 (Model C-321 of Denki Kagaku Keiki Co.), which was covered with a porous Teflon membrane 2' (pore size; 0.5 micron, Type FH of Millipore Ltd.), whereby the layer of the microorganisms was confined between the two membranes 2 and 4. Then these membranes were covered with Nylon net of which upper part was fastened with rubber rings 5 as illustrated in FIG. 1. A continuous measuring system as shown in FIG. 3 was assembled with the microbial electrode.

Figure 8:
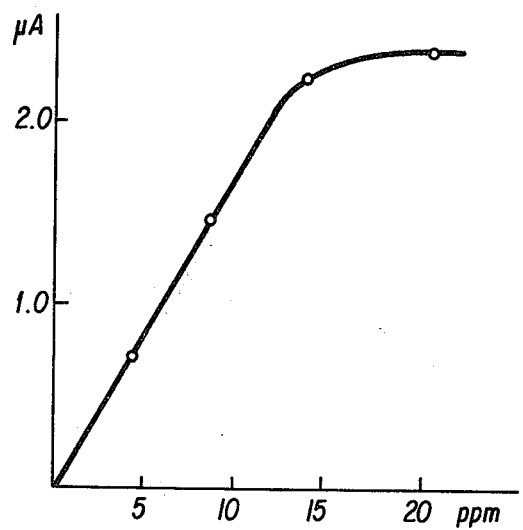
FIGS. 8 and 10 are charts which indicate the relationship between the ammonia concentration and the current decrease ($\mu A$).

For measurement, 0.05 M $Na_2HPO_4$-NaOH buffer solution (pH 10.0) was flowed at a flow rate of 3.9 ml/min., while blowing air into it at a rate of 3.9 ml/min. Then ammonia solution containing 0.1% glucose were injected with various concentration at a interval of 15 minutes with pulse width of 6 minutes, whereby the relationship between the current decrease in steady state and the concentration was examined. The results are shown in FIG. 8, in which the axis of abscissa represents the concentration of ammonia in the flow cell obtained by the conventional method and the axis of ordinate represents the current decrease ($\mu A$) in steady state.

A linear relationship was observed between the current decrease and the concentration of ammonia below 15 ppm. Stability of the microbial electrode was tested by feeding ammonia solution (90 ppm) automatically with pulse width of 6 minutes at a 30 minutes interval in this continuous determination system. The results are given in FIG. 9 which shows that no change was observed during a continuous operation of more than 10 days.

The selectivity of the microbial electrode for ammonia was also examined in the same manner as described above for more than 10 days. Table 4 shows the selectivity of the electrode. The microbial sensor did not respond to organic compounds such as glucose, acetic acid and glutamic acid for more than 10 days.

TABLE 4

| Selectivity of the microbial electrode | | |
|---|---|---|
| Material | Concentration (ppm) | Current difference ($\mu A$) |
| Ammonia | 90 | 1.9 |
| Glucose | 1000 | 0 |
| Acetic acid | 1000 | 0 |
| Ethanol | 1000 | 0 |
| Glutamic acid | 1000 | 0 |

EXAMPLE 3

Figure 2:
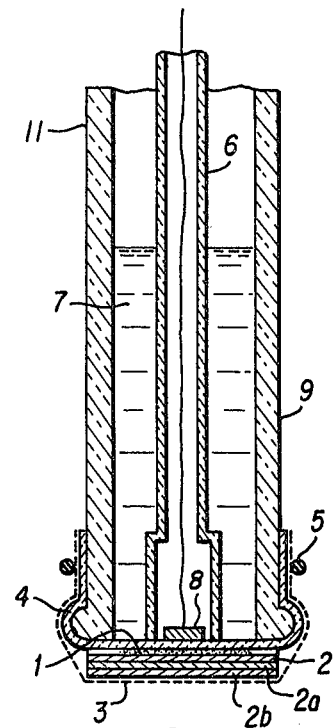
FIG. 2 is a simplified elevational section view of another microbial electrode indicated in EXAMPLE 3.

A microbial electrode 11 as illustrated in FIG. 2 was assembled in a similar manner as described in Example 1, which is another type of the microbial electrode according to the present invention.

The intact wet cells of the nitrifying bacteria obtained from 5.0 ml cultured broth obtained in the same manner as described in Example 1 were smeared on the porous Teflon membrane 2 (pore size: 0.5 micron, FH-Type of Millipore Ltd.). Then the Teflon membrane was cut in circle (diameter: 47 mm) and adhered on the diaphragm membrane 4 of the Galvanic-type oxygen sensitive electrode so that the microbial layer 1 was trapped between two membranes. A filter paper 2-a containing 0.05 M, $Na_2HPO_4$-NaOH buffer solution (pH 10.0) and cation-permeable membrane 2-b (CMV-type of Selemion membrane, Trademark of Asahi Glass Co., Inc.) were cut in circle (diameter: 47 mm) and put on the Teflon membrane 2 in order, respectively. These membranes were then covered with Nylon net 3 and the upper part was fixed with a rubber ring 5 to obtain the microbial electrode 11.

Figure 9:
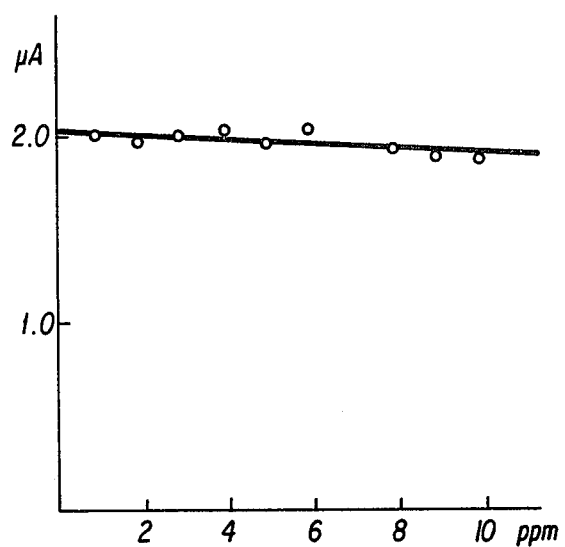
FIG. 9 is a chart indicating the stability of the microbial electrode of FIG. 1.
Figure 10:
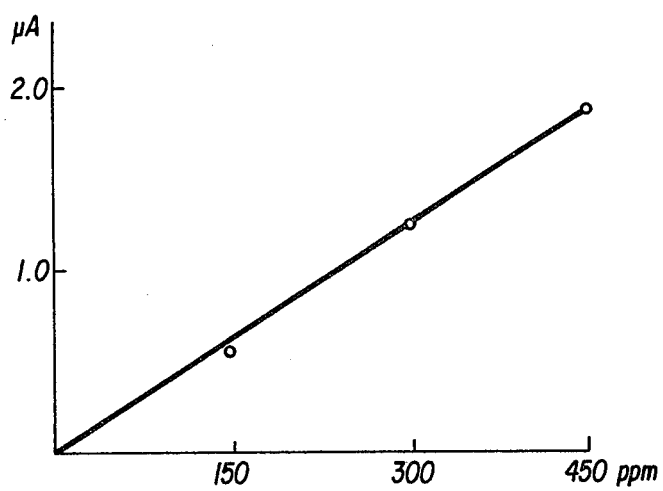

For measurement, 0.05 M phosphate buffer solution (pH 7.0) was flowed as a carrier liquid and ammonia solution was injected with various concentration in the same manner as described in Example 1. FIG. 9 shows calibration curves of the microbial electrode, in which the axis of abscissa represents ammonia concentration (ppm) and the axis of ordinate represents current decrease in steady state ($\mu A$). A linear relationship was observed between them.

What is claimed as new and desired to be secured by Letters Patent of the United States is:

1. A method for determining ammonia concentration in an aqueous liquid which contains dissolved oxygen, which comprises:
    (a) Contacting a sample of said liquid with a microbial electrode comprising:
      an oxygen-sensitive electrode having a diaphragm, bacteria capable of oxidizing ammonium ion and thereby consuming oxygen in direct or close contact with the diaphragm of said oxygen sensitive electrode, said bacteria being confined or immobilized by a porous membrane permeable to ammonia and to oxygen and impermeable to microbial cells; and (b) electrochemically sensing the rate of consumption or their decrease in steady state concentration of said oxygen caused by said microorganisms, and thereby (c) detecting the concentration of ammonia from said rate or said decrease of the oxygen.

2. A method as set forth in claim 1 wherein said membrane is selectively permeable to ammonia gas or to cations and said bacteria are held between the diaphragm of the electrode and said membrane covering the diaphragm.

3. A method as set forth in claim 1 wherein said sample solution is saturated with oxygen during the determination.

4. The method of claim 1 wherein said bacteria comprise those capable of oxidizing ammonia to form nitrous acid therefrom.

5. The method of claim 4 wherein said bacteria also comprise bacteria capable of oxidizing nitrous acid to form nitric acid therefrom.

6. The method of claim 5 wherein said bacteria are selected from the group consisting of *Nitrobacter winogradski* and *Nitrocystis sarcinoides*.

7. The method of claim 4 wherein said bacteria are selected from the group consisting of *Nitrosomonas monocella, Nitrosococcus nitrosus, Nitrosopira briensis, Nitrososocystis javanensis, Nitrosogloea merismoides*.

8. The method of claim 1 wherein said bacteria are selected from the group consisting of *Nitrosomonas europaea* ATCC 19718 and *Nitrobacter agilis* ATCC 14123 and mixtures thereof.

9. An ammonia-detecting electrode which comprises:
an oxygen-sensitive electrode having a diaphragm;
bacteria capable of oxidizing ammonium ion and thereby consuming oxygen in direct or close contact with the diaphragm of said oxygen sensitive electrode;
said bacteria being confined or immobilized by a porous membrane permeable to ammonia or ammonium ions and to oxygen, and impermeable to microbial cells.

10. The electrode of claim 9 wherein said membrane is selectively permeable to ammonia gas or to ions thereof and said bacteria are held between the diaphragm of the electrode and said membrane covering the diaphragm.

11. The electrode of claim 9 wherein said bacteria comprise those capable of oxidizing ammonia to form nitrous acid therefrom.

12. The method of claim 11 wherein said bacteria are selected from the group consisting of *Nitrosomonas monocella, Nitrosococcus nitrosus, Nitrosospira briensis, Nitrososocystis javanensis, Nitrosogloea merismoides*.

13. The method of claim 9 wherein said bacteria also comprise bacteria capable of oxidizing nitrous acid to form nitric acid therefrom.

14. The electrode of claim 13 wherein said bacteria are selected from the group consisting of *Nitrobacter winogradski* and *Nitrocystis sarcinoides*.

15. The electrode of claim 9 wherein said bacteria are selected from the group consisting of *Nitrosomonas europaea* ATCC 19718 and *Nitrobacter agilis* ATCC 14123.

* * * * *